(12) United States Patent
Chen et al.

(10) Patent No.: US 9,855,412 B2
(45) Date of Patent: Jan. 2, 2018

(54) NEEDLELESS CONNECTOR MODULE

(71) Applicant: LILY MEDICAL CORPORATION, Miao-Li Hsien (TW)

(72) Inventors: Chih-Lung Chen, Miaoli County (TW); Wei Hsuan Chang, Miaoli County (TW); Chih-Wei Chiu, Miaoli County (TW)

(73) Assignee: LILY MEDICAL CORPORATION, Miao-Li Hsien (TW)

( * ) Notice: Subject to any disclaimer, the term of this patent is extended or adjusted under 35 U.S.C. 154(b) by 468 days.

(21) Appl. No.: 14/450,360

(22) Filed: Aug. 4, 2014

(65) Prior Publication Data

US 2015/0157800 A1 Jun. 11, 2015

(30) Foreign Application Priority Data

Dec. 11, 2013 (TW) .................................. 102223378

(51) Int. Cl.
| | |
|---|---|
| *A61M 5/30* | (2006.01) |
| *A61M 39/26* | (2006.01) |
| *A61M 39/10* | (2006.01) |
| *A61M 39/16* | (2006.01) |
| *A61M 39/22* | (2006.01) |

(Continued)

(52) U.S. Cl.
CPC ............ *A61M 39/26* (2013.01); *A61M 39/10* (2013.01); *A61M 39/16* (2013.01); *A61M 39/223* (2013.01); *A61M 39/18* (2013.01); *A61M 2039/0633* (2013.01); *A61M 2039/1027* (2013.01); *A61M 2039/246* (2013.01); *A61M 2039/2433* (2013.01);

(Continued)

(58) Field of Classification Search
CPC ...... A61M 2039/267; A61M 2039/268; A61M 2039/2433; A61M 2039/2446; A61M 2039/246; A61M 2039/1027; A61M 2039/0633; A61M 39/26; A61M 39/10; A61M 39/16

See application file for complete search history.

(56) References Cited

U.S. PATENT DOCUMENTS

| 2002/0032433 A1* | 3/2002 | Lopez ..................... A61M 5/14 604/533 |
|---|---|---|
| 2010/0249724 A1* | 9/2010 | Cote, Sr. ............... A61M 39/26 604/249 |

(Continued)

*Primary Examiner* — Nathan R Price
*Assistant Examiner* — Anh Bui
(74) *Attorney, Agent, or Firm* — Li & Cai Intellectual Property (USA) Office

(57) ABSTRACT

A needleless connector module comprises: a sleeve tube, an elastic valve, a flow guiding unit and an extension unit. The elastic valve sleeves a guiding tube of the flow guiding unit. A hollow shoulder portion of the elastic valve abuts a slanted retaining wall of the sleeve tube. Under a first usage condition, the hollow head portion of the elastic valve encloses the guiding tube narrow portion, hiding the first guiding opening in the airtight seam. Under a second usage condition, an injection tube presses the top face of the elastic valve, a hollow head portion of the elastic valve presses downward, driving the valve inner wall to abut a waist platform formed on the guiding tube, such that the first guiding opening is exposed outside the airtight seam, and such that the first guiding opening is connected to an injection opening of the injection tube.

12 Claims, 12 Drawing Sheets

(51) Int. Cl.
*A61M 39/24* (2006.01)
*A61M 39/06* (2006.01)
*A61M 39/18* (2006.01)

(52) U.S. Cl.
CPC ............... *A61M 2039/2446* (2013.01); *A61M 2039/267* (2013.01); *A61M 2039/268* (2013.01)

(56) References Cited

U.S. PATENT DOCUMENTS

2011/0282302 A1* 11/2011 Lopez .................. A61M 39/10
604/247
2015/0157799 A1* 6/2015 Chen ..................... A61M 39/26
604/68

* cited by examiner

NEEDLELESS CONNECTOR MODULE

BACKGROUND OF THE INVENTION

1. Field of the Invention

The present disclosure relates to a needleless connector module; in particular, to a needleless connector module for injector devices, for improving air-tight effect of its components, thereby preventing leaking of air and liquid and backflows. Additionally the structure of the present disclosure allows better implementation of sterilization and waste disposal of the present disclosure after use.

2. Description of Related Art

Conventional injector devices have needles and plungers. The pushing of the plunger expels liquid which flows through the needle and into the object to be injected. However, used and discarded needles are sharp and therefore dangerous. Needles used to inject living objects also have risks of contacting and carrying infections. Waste disposal regarding needles is a problematic issue. Needles are one-use items and must be discarded are use in order to prevent growth of bacteria or other infection problems. This creates problems for public health safety, environmental burden and costs.

In light of the above, needleless injector devices are created. However, needleless injector devices are poor at being airtight and preventing leakage, even allowing backflows. Using complicated structures to solve the abovementioned problems creates difficulty in producing complicated molds and increasing development costs.

Additionally, conventional needleless injector devices have enclosures which limit the effects of sterilization, imposing risks to public health safety. Also, when using the needleless injector device, other assembly tube units are used. However, molds are difficult to produce, and structures are difficult to fully complement each other, so assembly other tube units is difficult in practice. Not only is the quality hard to maintain, but sterilization is hard to maintain during assembly, thereby a satisfying level of standard is difficult to achieve. Moreover, in order to keep needleless injector devices bacteria free, the structures of the needleless injector devices are often more enclosed. However, this design also causes unreachable regions during sterilization, leading to spread of infection and risk to public health safety.

Hence, the present inventor believes the above mentioned disadvantages can be overcome, and through devoted research combined with application of theory, finally proposes the present disclosure which has a reasonable design and effectively improves upon the above mentioned disadvantages.

SUMMARY OF THE INVENTION

The object of the present disclosure is to provide a needleless connector module which achieves the effects of being airtight, preventing leakage and being bacteria free through a relatively simple structure. The mold is simplified to reduce production cost. The product have increased yield rate of good production while having good expandability. Additionally, a bacteria free environment can be maintained while allowing thorough sterilization, beneficial to public health safety.

In order to achieve the aforementioned objects, the present disclosure provides a needleless connector module, including: a sleeve tube, an elastic valve, a flow guiding unit, and an extension unit. The sleeve tube has a first opening formed at the lower end of the sleeve tube, a second opening formed at the upper end of the sleeve tube, and a first inner wall. The first inner wall tapers toward the upper end of the sleeve tube and a slanted retaining wall is defined at the upper end of the first inner wall. A second inner wall extends from the slanted retaining wall toward the upper end of the sleeve tube. The slanted retaining wall and the second inner wall define an upper compartment. The first inner wall defines a lower compartment. The elastic valve has a valve inner wall and includes, from top to bottom, a hollow head portion, a hollow shoulder portion, and a hollow base portion. The upper compartment accommodates the hollow head portion. The lower compartment accommodates the hollow base portion. The hollow base portion tapers toward the hollow head portion and the hollow shoulder portion is formed therebetween. A top surface of the hollow head portion is formed with an airtight seam. The top surface is for connecting to an injection tube. The flow guiding unit includes: a bottom cover main body having a guiding tube passing from an outer face of the bottom cover main body to an inner face of the bottom cover main body, wherein the guiding tube protrudes and extends from the inner face, the guiding tube has a first guiding opening, the guiding tube is in fluid communication with a second guiding opening at the outer face, and the bottom cover main body is formed with a guiding hole passing from the outer face to the inner face; a welded portion positioned on the outer face; a waist platform formed at the outer wall of the guiding tube, wherein the waist platform and the first guiding opening define a guiding tube narrow portion therebetween, and the waist platform and the inner face define a guiding tube wide portion therebetween; and a plurality of bottom cover ribs formed on the inner face. The extension unit has at least a main tubing. The extension unit is connected to the outer face through the welded portion, such that the main tubing is connected to the second guiding opening and a gap exists between the extension unit and the outer face. The gap is in fluid communication with the guiding hole. The elastic valve sleeves the guiding tube, and the hollow shoulder portion abuts the slanted retaining wall, such that the elastic valve and the flow guiding unit are assembled together in the sleeve tube, and such that the first opening is sealed by the bottom cover main body. Selectively under a first usage condition, the inner wall of the hollow head portion encloses the guiding tube narrow portion, thereby the first guiding opening is hidden in the airtight seam. Under a second usage condition, the injection tube abuts the top surface, such that the hollow head portion is pressed downward, driving the inner wall of the valve body to abut the waist platform, and such that the first guiding opening is exposed outside the airtight seam, thereby the first guiding opening can be connected to an injection opening of the injection tube.

In order to achieve the aforementioned objects, the present disclosure provides a needleless connector module, including: a sleeve tube, an elastic valve, a flow guiding unit, and an extension unit. The sleeve tube has a first opening formed at the lower end of the sleeve tube, a second opening formed at the upper end of the sleeve tube, and a first inner wall. The first inner wall tapers toward the upper end of the sleeve tube and a slanted retaining wall is defined at the upper end of the first inner wall. A second inner wall extends from the slanted retaining wall toward the upper end of the sleeve tube. The slanted retaining wall and the second inner wall define an upper compartment. The first inner wall defines a lower compartment. The elastic valve has a valve inner wall and includes, from top to bottom, a hollow head portion, a hollow shoulder portion, and a hollow base portion. The upper compartment accommodates the hollow head portion. The lower compartment accommodates the hollow base portion. The hollow base portion tapers toward the hollow head portion and a hollow shoulder portion is formed therebetween. A top surface of the hollow head portion is formed with an airtight seam. The top surface is for abutting an injection tube. The flow guiding unit includes: a bottom cover main body having a guiding tube passing from an outer face of the bottom cover main body to an inner face of the bottom cover main body, wherein the guiding tube protrudes and extends from the inner face, the guiding tube has a first guiding opening, the guiding tube is in fluid communication with a second guiding opening at the outer face, and the bottom cover main body is formed with a guiding hole passing from the outer face to the inner face; a welded portion positioned on the outer face; a waist platform formed at the outer wall of the guiding tube, wherein the waist platform and the first guiding opening define a guiding tube narrow portion therebetween, and the waist platform and the inner face define a guiding tube wide portion therebetween; and a plurality of bottom cover ribs formed on the inner face. The extension unit has at least a main tubing. The extension unit is connected to the outer face through the welded portion, such that the main tubing is connected to the second guiding opening and the main tubing is surrounded by an external space. The guiding hole passes through the top portion of the extension unit and is in fluid communication with the external space. The elastic valve sleeves the guiding tube, and the hollow shoulder portion abuts the slanted retaining wall, such that the elastic valve and the flow guiding unit are assembled together in the sleeve tube, and such that the first opening is sealed by the bottom cover main body. Selectively under a first usage condition, the inner wall of the hollow head portion encloses the guiding tube narrow portion, thereby the first guiding opening is hidden in the airtight seam. Under a second usage condition, the injection tube abuts the top surface, such that the hollow head portion is pressed downward, driving the inner wall of the valve body to abut the waist platform, and such that the first guiding opening is exposed outside the airtight seam, thereby the first guiding opening can be connected to an injection opening of the injection tube.

Through the abovementioned technical features, the present disclosure can effectively simplify molding and reduce production cost, while maintaining an airtight, leak-free and bacteria-free environment and taking care that sterilization can be carried out.

In order to further the understanding regarding the present disclosure, the following embodiments are provided along with illustrations to facilitate the disclosure of the present disclosure.

DETAILED DESCRIPTION OF THE PREFERRED EMBODIMENTS

First Embodiment

Figure 1A:
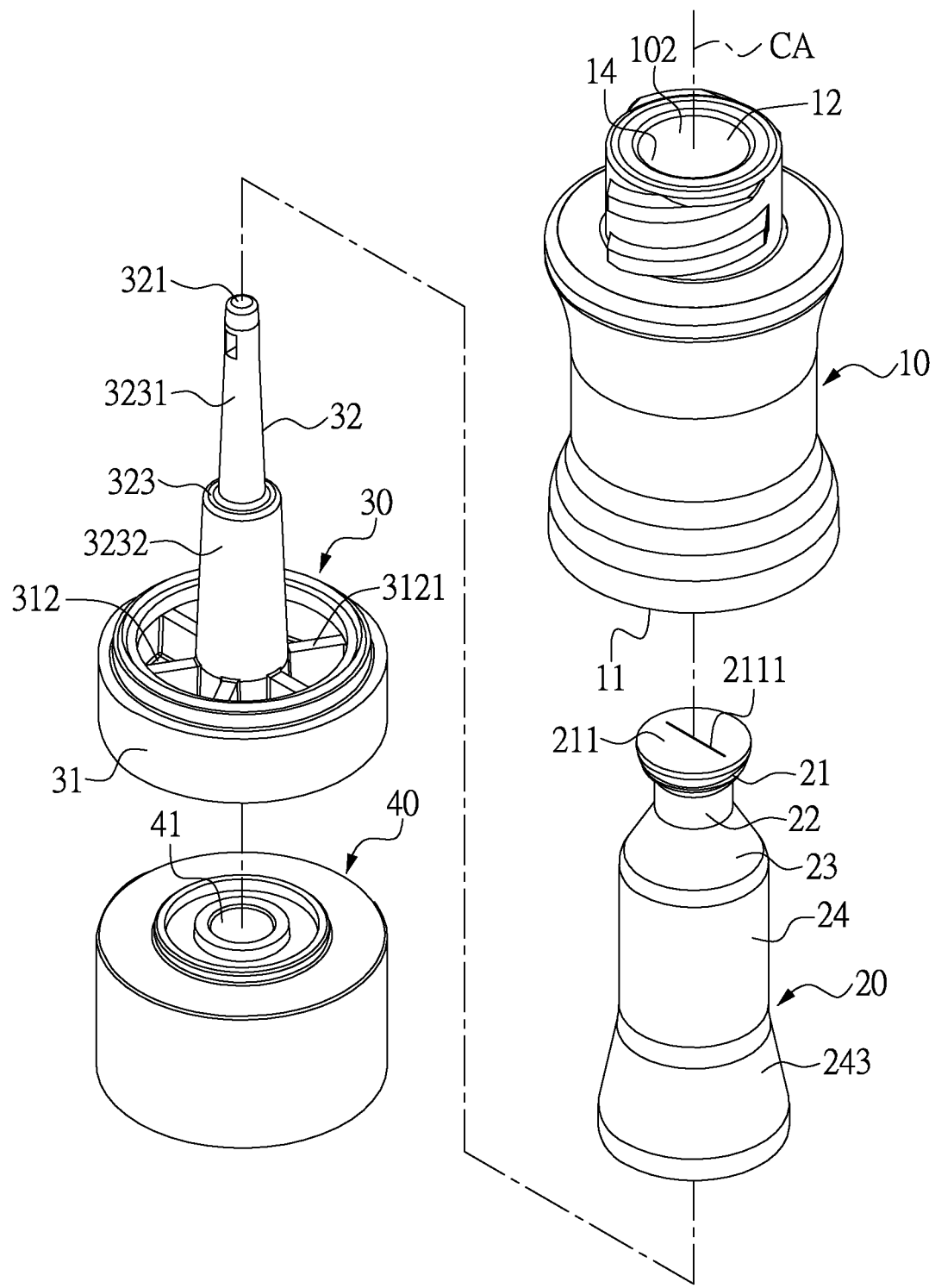
FIG. 1A shows an exploded view from above of a needleless connector module according to the present disclosure.
Figure 1B:
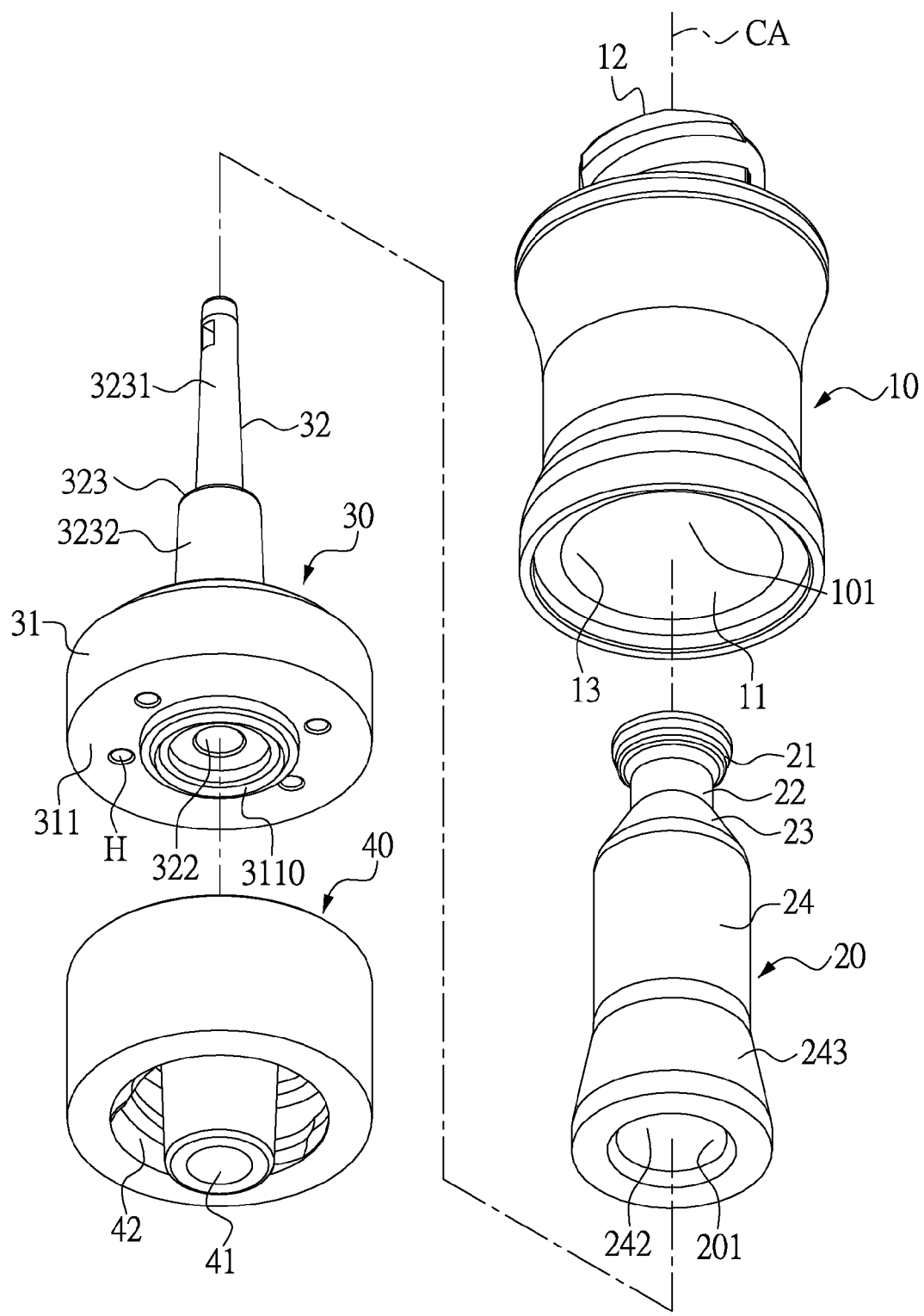
FIG. 1B shows an exploded view from below of a needleless connector module according to the present disclosure.
Figure 1C:
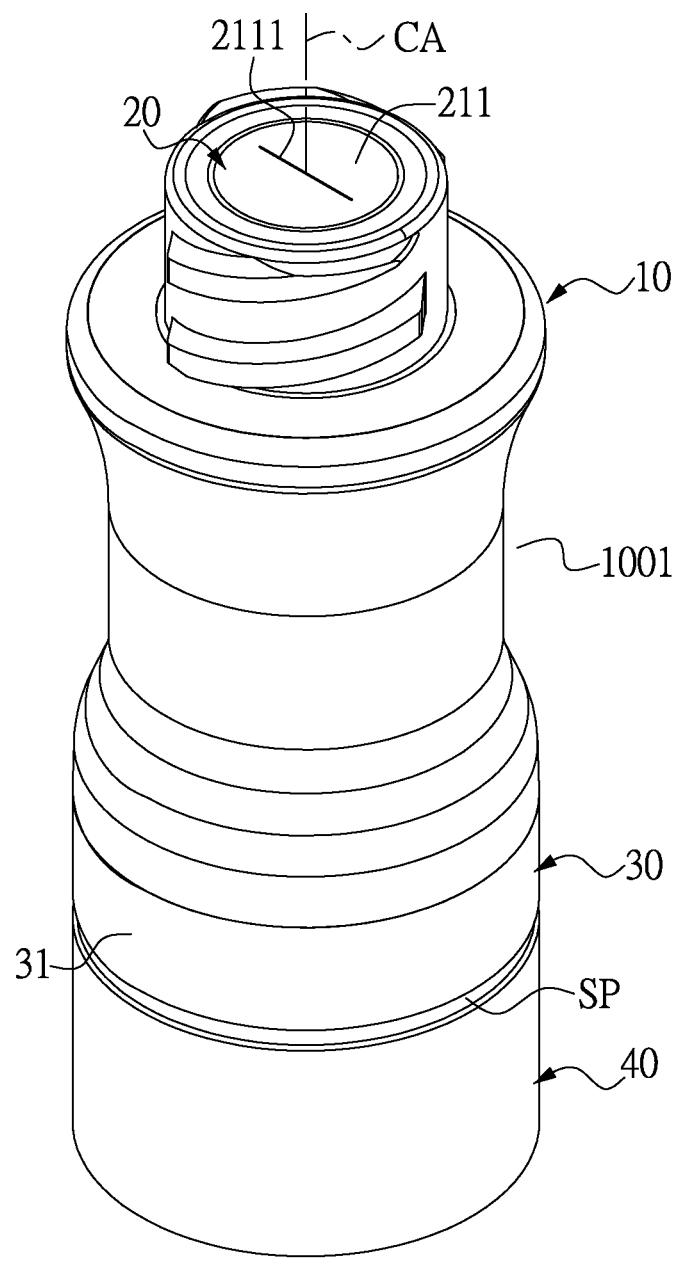
FIG. 1C shows a perspective view from above of an assembled needleless connector module according to the present disclosure.
Figure 1D:
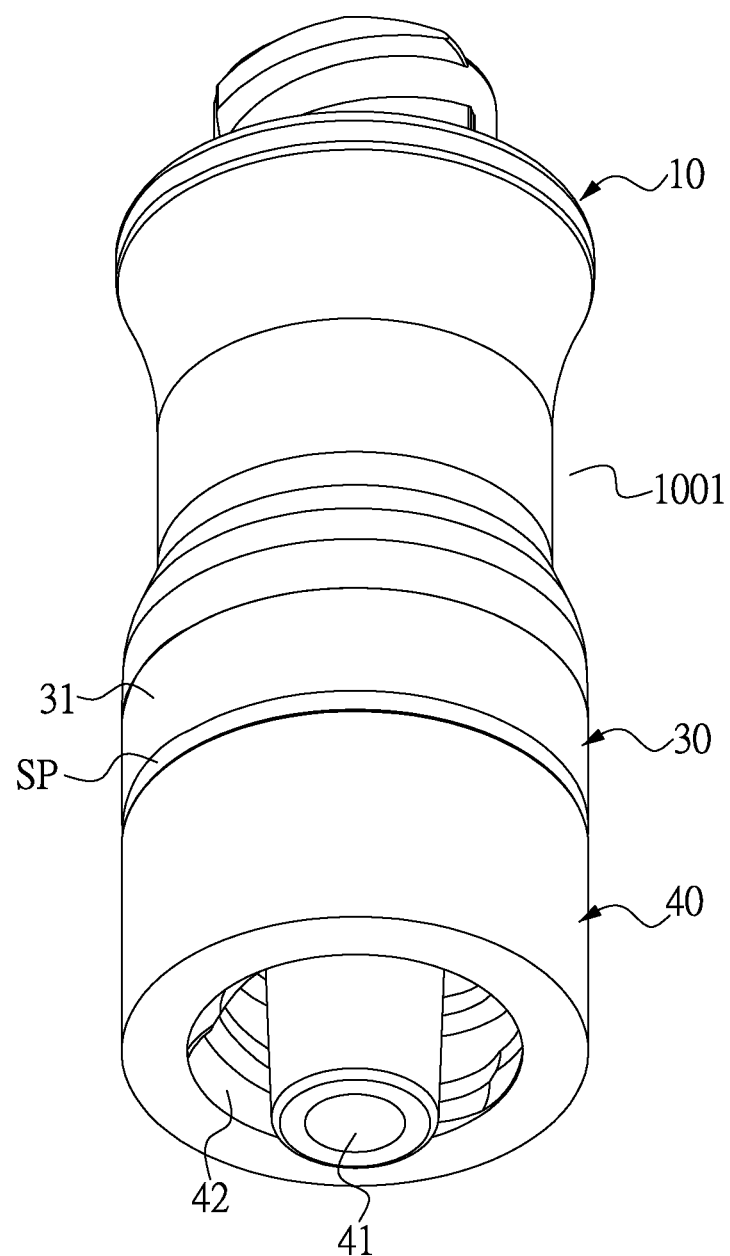
FIG. 1D shows a perspective view from below of an assembled needleless connector module according to the present disclosure.

Referring to FIG. 1A, FIG. 1B, FIG. 1C and FIG. 1D, the present disclosure provides a needleless connector module, including: a sleeve tube 10, an elastic valve 20, a flow guiding unit 30, and an extension unit 40.

The sleeve tube 10 is substantially hollow and the two ends thereof are in fluid communication. Therefore, a first opening 11 is formed at the lower end of the sleeve tube 10, and a second opening 12 and a first inner wall 13 is formed at the upper end of the sleeve tube 10. The first inner wall 13 tapers toward the upper end of the sleeve tube 10 and a slanted retaining wall 131 is defined at the upper end of the first inner wall 13. A second inner wall 14 extends from the slanted retaining wall 131 toward the upper end of the sleeve tube 10. The slanted retaining wall 131 and the second inner wall 14 define an upper compartment 102. The first inner wall 13 defines a lower compartment 101. Additionally the outer portion of the sleeve tube 10 is formed with a receding portion 1001 to facilitate gripping.

The elastic valve 20 is preferably made of silicone but is not limited thereto. The elastic valve 20 has a valve inner wall 201 and includes, from top to bottom, a hollow head portion 21, a hollow shoulder portion 23, and a hollow base portion 24. The upper compartment 102 of the sleeve tube 10 accommodates the hollow head portion 21. The lower compartment 101 accommodates the hollow base portion 24. The hollow base portion 24 tapers toward the hollow head portion 21 and the hollow shoulder portion 23 is formed therebetween. A top surface 211 of the hollow head portion 21 is formed with an airtight seam 2111. The airtight seam 2111 is normally closed. When the airtight seam 2111 is stretched open, the hollow head portion 21 is opened and the interior of the hollow head portion 21 is allowed to communicate with the exterior. Therefore when the top surface 211 is abutting an injection tube SY, the flow guiding unit 30 disposed inside the elastic valve 20 can be communicated with the injection tube SY through the stretched airtight seam 2111. The flow guiding unit 30 includes at least: a bottom cover main body 31, a welded portion 3110, a waist platform 323 and a plurality of bottom cover ribs 3121.

The bottom cover main body 31 has a guiding tube 32 passing from an outer face 311 of the bottom cover main body 31 to an inner face 312 of the bottom cover main body 31. The guiding tube 32 protrudes and extends from the inner face 312. The guiding tube 32 has a first guiding opening 321, and is in fluid communication with a second guiding opening 322 at the outer face 311. Additionally, the bottom cover main body 31 is formed with a guiding hole H passing from the outer face 311 to the inner face 312.

The welded portion 3110 is positioned on the outer face 311. The welded portion 3110 can be welded by ultrasonic waves to other external units. The waist platform 323 is formed at the outer wall of the guiding tube 32 in a horizontally protruding manner, such that the waist platform 323 and the first guiding opening 321 define a guiding tube narrow portion 3231 therebetween. The waist platform 323 extends along the direction of the longitudinal central axis CA of the guiding tube 32, and a guiding tube wide portion 3232 is defined between the inner face waist platform 323 and the inner face 312.

The bottom cover ribs 3121, as shown in the present embodiment, are preferably six radially arranged spokes but are not limited thereto. The bottom cover ribs 3121 are formed on the inner face 312 for providing structural strength, such that when the welded portion 3110 of the outer face 311 is being welded by ultrasound waves, the board (label omitted) defined between the outer face 311 and the inner face 312 does not become disfigured or deformed due to high temperature, thereby increasing the yield rate of good production.

The extension unit 40 has at least a main tubing 41. The extension unit 40 is connected to the outer face 311 through the welded portion 3110, such that the main tubing 41 is connected to the second guiding opening 322, and a gap SP exists between the extension unit 40 and the outer face 311 after welding. The gap SP is in fluid communication with the guiding hole H, such that pressurized steam can easily enter the sleeve tube 10 during sterilization, thereby properly sterilizing biohazard material. When the elastic valve 20 sleeves the guiding tube 32 of the flow guiding unit 30, the hollow shoulder portion 23 of the elastic valve 20 is slanted and therefore can abut and be retained by the slanted retaining wall 131 inside the sleeve tube 10, such that the elastic valve 20 and the flow guiding unit 30 can be disposed in the sleeve tube 10 together, and such that the first opening 11 of the sleeve tube 10 is sealed by the bottom cover main body 31.

According to the abovementioned structure of the present disclosure, when the present disclosure is selectively under a first usage condition, the inner wall of the hollow head portion 21 encloses the guiding tube narrow portion 3231, thereby the first guiding opening 321 is hidden in the airtight seam 2111. Under a second usage condition, the injection tube SY abuts the top surface 211 of the elastic valve 20, such that the hollow head portion 21 is pressed downward, driving the valve inner wall 201 to abut the waist platform 323, and such that the first guiding opening 321 is exposed outside the airtight seam 2111, thereby the first guiding opening 321 can be connected to an injection opening (label omitted) of the injection tube SY, completing the connection of the needleless connector.

Preferably, the valve inner wall 201 includes a base portion inner wall 241 formed at the hollow base portion 24. Under the abovementioned second usage condition, the elastic valve 20 is deformed due to pressure, causing the base portion inner wall 241 to interfere and abut the waist platform 323. By this configuration, when the elastic valve 20 is pressed downward, through the interference of the base portion inner wall 241 to the waist platform 323, the base portion inner wall 241 and the waist platform 323 press against each other, such that the top surface 211 of the elastic valve 20 has a preferred resilient effect against the injection tube SY which it presses against, ensuring an airtight abutment between the top surface 211 of the elastic valve 20 and the injection tube SY. When the injection tube SY is removed, the force provided on the elastic valve 20 by the waist platform 323 results in preferred restoration of the elastic valve 20 after being deformed by pressure. These features increase the life span of the present disclosure and have a positive effect on the stability of connected injection tube SY.

Specifically, the base portion inner wall 241 includes a side base portion inner wall 2411 and an interference inner wall 2412. The interference inner wall 2412 extends the side base portion inner wall 2411 toward the longitudinal central axis CA of the sleeve tube 10 and is proximal to the hollow shoulder portion 23. Therefore, under the second usage condition, the interference inner wall 2412 abuts surely against the waist platform 323, such that the waist platform 323 can push back against the interference inner wall 2412 and in turn the elastic valve 20 has a preferred resilient effect against the injection tube SY. Aside from increasing the resilience of the elastic valve 20 through the waist platform 323, the elastic valve 20 is formed with an expansion portion 243 extending outward (away from the central axis CA of the sleeve tube 10) at a portion of the hollow base portion 24 proximal to the bottom cover main body 31, such that under the second usage condition the present disclosure can also increase the resilience effect through the abutment of the expansion portion 243 to the inner wall of the sleeve tube 10.

Preferably, in order for the waist platform 323 to not prevent the elastic valve 20 from entering the sleeve tube 10, a first compression space P1 is defined in the hollow base portion 24 and between the interference inner wall 2412, a portion of the side base portion inner wall 2411, the waist platform 323 and the guiding tube narrow portion 3231 when the present disclosure is under the first usage condition, for adjusting the overall contact surface of the valve inner wall 201 to the guiding tube narrow portion 3231, guiding tube wide portion 3232 and waist platform 32, in turn adjust the force required to press the elastic valve 20 into the sleeve tube 10. Additionally, preferably, the surface of the valve inner wall 201 of the elastic valve 20 can be formed with rough pattern (not shown in the figures). The rough pattern is a microstructure of granulated indentations on the surface formed through sandblasting. The unevenness of the rough pattern decreases the contact surface between itself and other units, thereby decreasing frictional force. Particularly, this microstructure can be formed on the inner wall of the hollow head portion 21, such that when the elastic valve 20 is pressed downward, the first guiding opening 321 of the guiding tube 32 has less friction with the inner wall of the hollow head portion 21. In other words, the first guiding opening 321 is more easily passed through the airtight seam 2111, and exposed outside the airtight seam 2111 under the second usage condition. Additionally, when removing the injection tube SY and returning to the first usage condition, smaller friction between the inner wall of the hollow head portion 21 and the guiding tube 10 causes the hollow head portion 21 to more surely return to its original shape and enclose the first guiding opening 321, preventing contamination of the first guiding opening 321.

Likewise, the outer wall of the elastic valve 20 can also be treated with sandblasting, such that the friction between the elastic valve 20 and the sleeve tube 10 is decreased, allowing the elastic valve 20 to be smoothly deformed and restored. After sandblasting treatment, the stress of the surface of the elastic valve 20 is reduced. Under this state, the elastic valve 20 is more easily deformed and restored, assisting the actuation of the elastic valve 20 during use. Compared to sandblasting treatment, likewise for reducing the influence of frictional forces on the deformation and actuation of the elastic valve 20, between the elastic valve 20 or the guiding tube 32 of the flow guiding unit 30 can be achieved through a method of coating silicone oil. After coating the silicone oil, at least a silicone oil layer (label omitted) can be formed between the elastic valve 20 or the guiding tube 32 of the flow guiding unit 30, for reducing friction between the two components, such that the elastic valve 20 can be easily deformed and restored between the first usage condition and the second usage condition. Restoring the elastic valve 20, in other words, is allowing the first guiding opening 321 to be surely enclosed under the first usage condition to eliminate potential pathogens and contamination from microbes, and therefore assists in raising the maintenance of the bacteria free environment of the present disclosure.

Additionally, of particular note, the bottom cover ribs 3121 are formed on the inner face 312 through the method of protruding arrangement. Therefore a support structure whose height is higher relative to the inner face 312 can be formed, and the end of the hollow base portion 24 of the elastic valve 20 proximal to the bottom cover main body 31 has an outer edge of a valve base portion opening 242. Therefore when the elastic valve 20 sleeves the flow guiding unit 30, the outer edge of the valve base portion opening 242 does not directly abut, or contact the inner face 312, and instead abuts the upper parts of the bottom cover ribs 3121. Therefore the elastic valve 20 can be elevated by the bottom cover ribs 3121, thereby the elastic valve 20 can be offset from the guiding hole H to prevent the guiding holes H from being blocked by the elastic valve 20 during sterilization. The elastic valve 20 expands due to heat. If the elastic valve 20 is not elevated, the guiding hole H may blocked. Additionally, when the elastic valve 20 is elevated, steam for sterilizing can more easily enter from under the elastic valve 20 into the region between the elastic valve 20 and the guiding tube 32, further preventing creation of blind spots during sterilization.

A hollow neck portion 22 can be formed between the hollow head portion 21 and the hollow shoulder portion 23 of the elastic valve 20 of the present disclosure. The outer wall of the hollow neck portion 22 contracts horizontally toward the central axis CA of the sleeve tube 10 relative to the hollow head portion 21 and the hollow shoulder portion 23, such that the hollow neck portion 22 and the inner wall of the upper compartment 102 of the sleeve tube 10 can define a second compression space P2. When the injection tube SY begins to abut the top surface 211 of the elastic valve 20, the second compression space P2 provides space for the hollow head portion 21 positioned in the upper compartment 102 to successfully stretched open by the injection tube SY and the guiding tube 32, such that the first guiding opening 321 is exposed from the airtight seam 2111 and connected to the injection tube SY.

Referring to FIG. 1A, FIG. 1B, FIG. 1C, FIG. 1D, FIG. 2A and FIG. 2B, the extension unit 40 of the present disclosure can take on different forms. One form is screw-type extension unit (label omitted). Therefore, besides the main tubing 41, a screw connection portion 42 can be arranged around the main tubing 41. When matched with a screw connection portion 42, the main tubing 41 can be connected to other external tubing (not shown in the figures) or containers (not shown in the figures) according to the needs of the user. Additionally, referring to FIG. 3A, the extension unit 40a be a plug-type extension unit (label omitted). The interior of the main tubing 41a of the plug-type extension unit has a plug portion (label omitted), such that the main tubing 41a can be plugged to external tubing through the plug portion. A preferred method for forming a plug portion is to have the tube diameter at one end of the main tubing 41a proximal to the second guiding opening (not shown in the figures) can expand toward the end distal from the second guiding opening (label omitted), such that the end of the main tubing 41a proximal to the second guiding opening is a relatively narrow plug portion, but is not limited thereto. As long as the external tubing and the main tubing 41a have different diameters and can be plugged to each other, a plugging connection can be produced with the main tubing 41a. Similarly, FIG. 3B and FIG. 3C respectively show a Y-type extension unit and a T-type extension unit, respectively having a main tubing 41b and a main tubing 41c. The midsection of the main tubings (41b, 41c) each have a plug portion (label omitted). The function of the plug portions is similar the plug portion of FIG. 3A, and can provide plugging to external tubing or containers. The portion of the main tubing (41b, 41c) between the plug portion and the end proximal to the second guiding opening can be connected to a branch tubing (42b, 42c). The difference between the branch tubing 42b and the branch tubing 42c lies in that, the branch tubing 42b and the main tubing 41b form a Y-shape structure, and the branch tubing 42c is perpendicular to the main tubing 41c to form a T-shape structure. Therefore, according to needs, dosages can be added or changed through the branch tubing (42b, 42c).

Figure 3A:
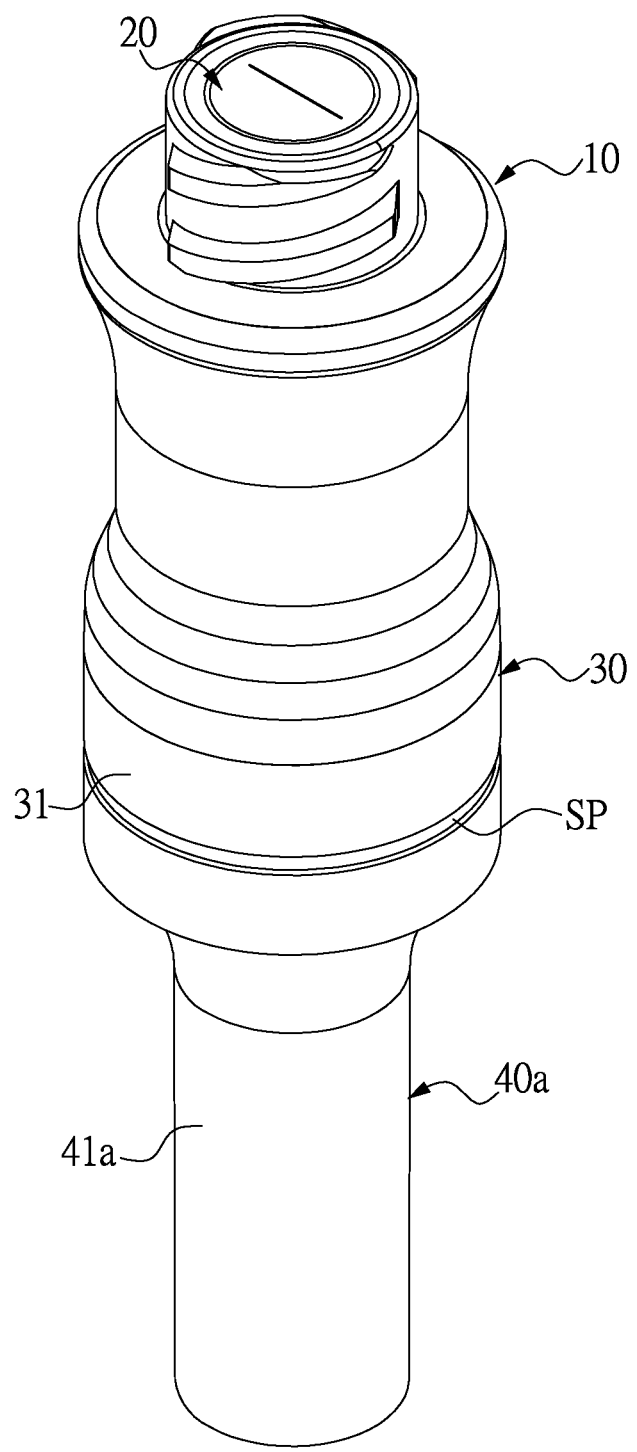
FIG. 3A shows a perspective view of a needleless connector module connected to another extension unit according to the present disclosure.
Figure 3B:
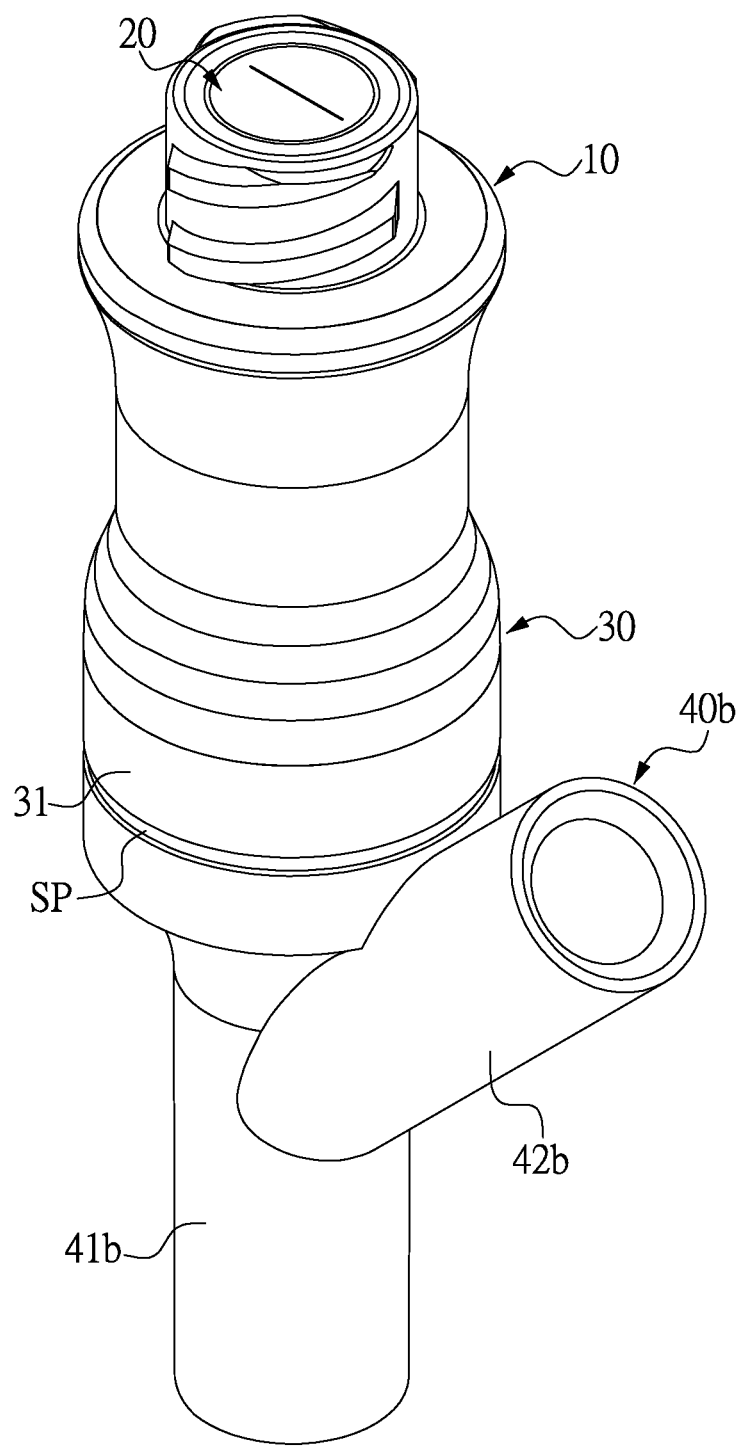
FIG. 3B shows a perspective view of a needleless connector module connected to another extension unit according to the present disclosure.
Figure 3C:
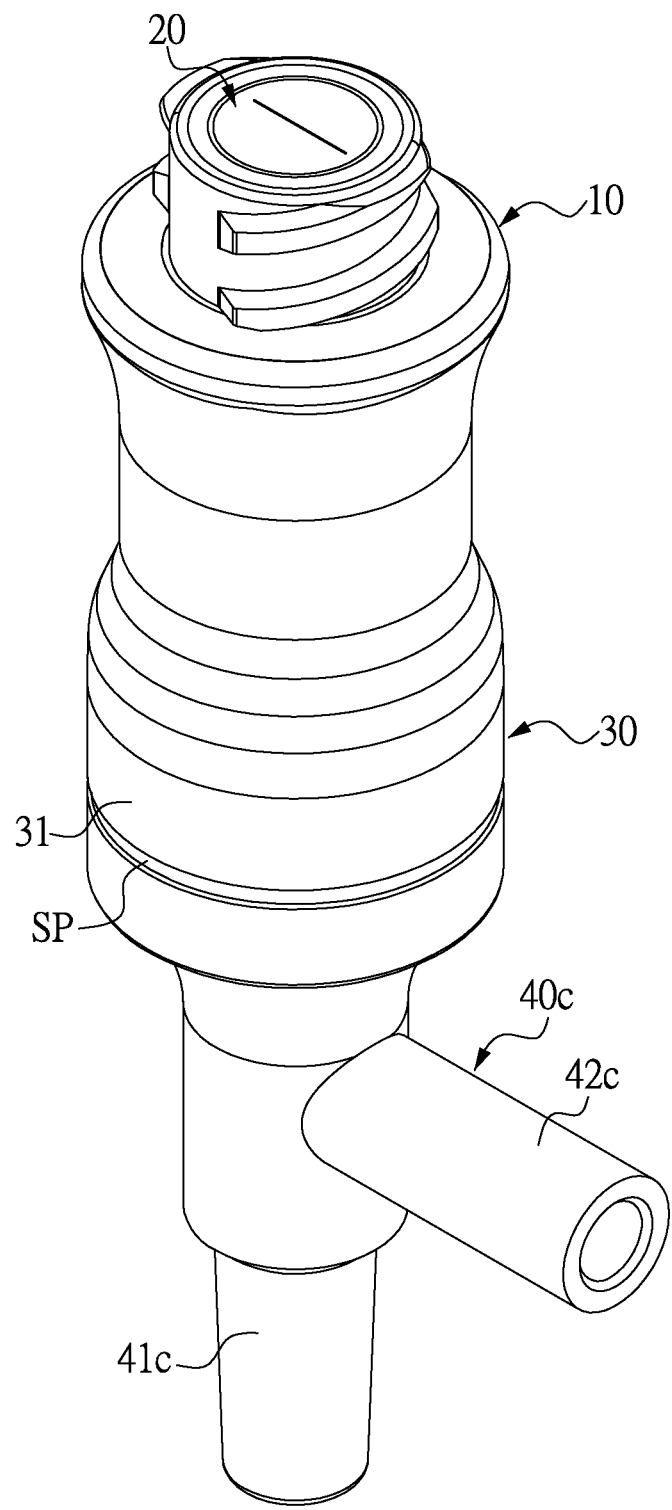
FIG. 3C shows a perspective view of a needleless connector module connected to another extension unit according to the present disclosure.
Figure 3D:
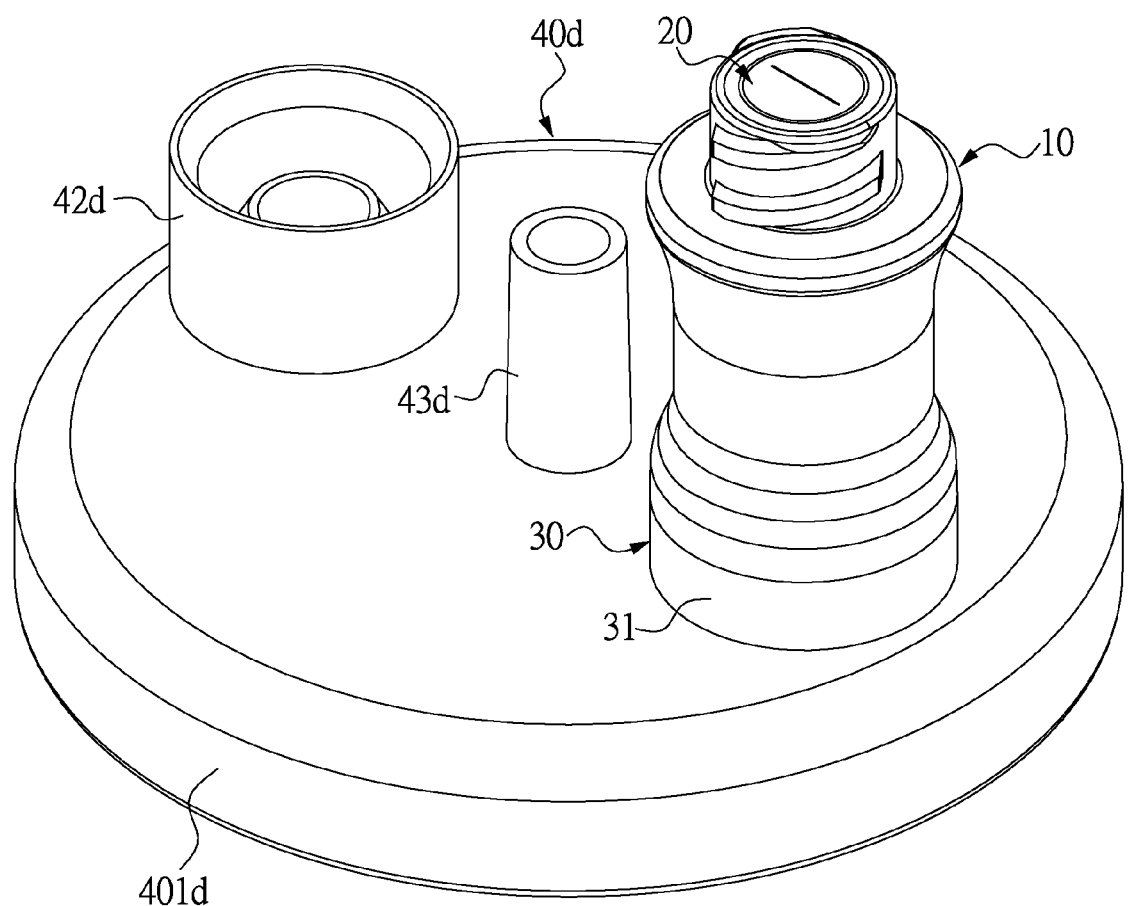
FIG. 3D shows a perspective view of a needleless connector module connected to another extension unit according to the present disclosure.

Referring to FIG. 3D, the extension unit 40d not only has a main tubing 41d, but also a top cover portion 401d. The main tubing 41d is formed at the top cover portion 401d. The top cover portion 401d is formed with a branch tubing 42d and a bacteria-free hole 43d, thereby forming a top-cover-type extension unit, which serves as a top cover which can cover a buffer tube (label omitted). The buffer tube can be used to retain dosages from intravenous drips, and through a connection assembly connect to a patient's body. The main tubing 41d can be welded with the welded portion (label omitted) of the surface (label omitted) of the top cover main body 31, thereby communicating with the second guiding opening (label omitted) of the flow guiding unit 30. The branch tubing 42d can communicate with an intravenous bag. The bacteria-free hole 43d can have a bacteria-free filter membrane disposed therein (not shown in the figures), such that the bacteria-free hole 43d maintains the pressure balance of the interior and exterior of the buffer tube and the bacteria-free condition in the buffer tube. Therefore through the top-cover-type extension unit of the present disclosure, dosages can be added via the main tubing according to situations during intravenous dripping. Of course, to facilitate sterilization, a gap exists between the bottom cover main body 31 and the top cover portion 401d of the present disclosure, such that pressurized steam can easily enter the sleeve tube 10 through the guiding hole (such as the guiding hole H of FIG. 1B). during sterilization.

Second Embodiment

Figure 2A:
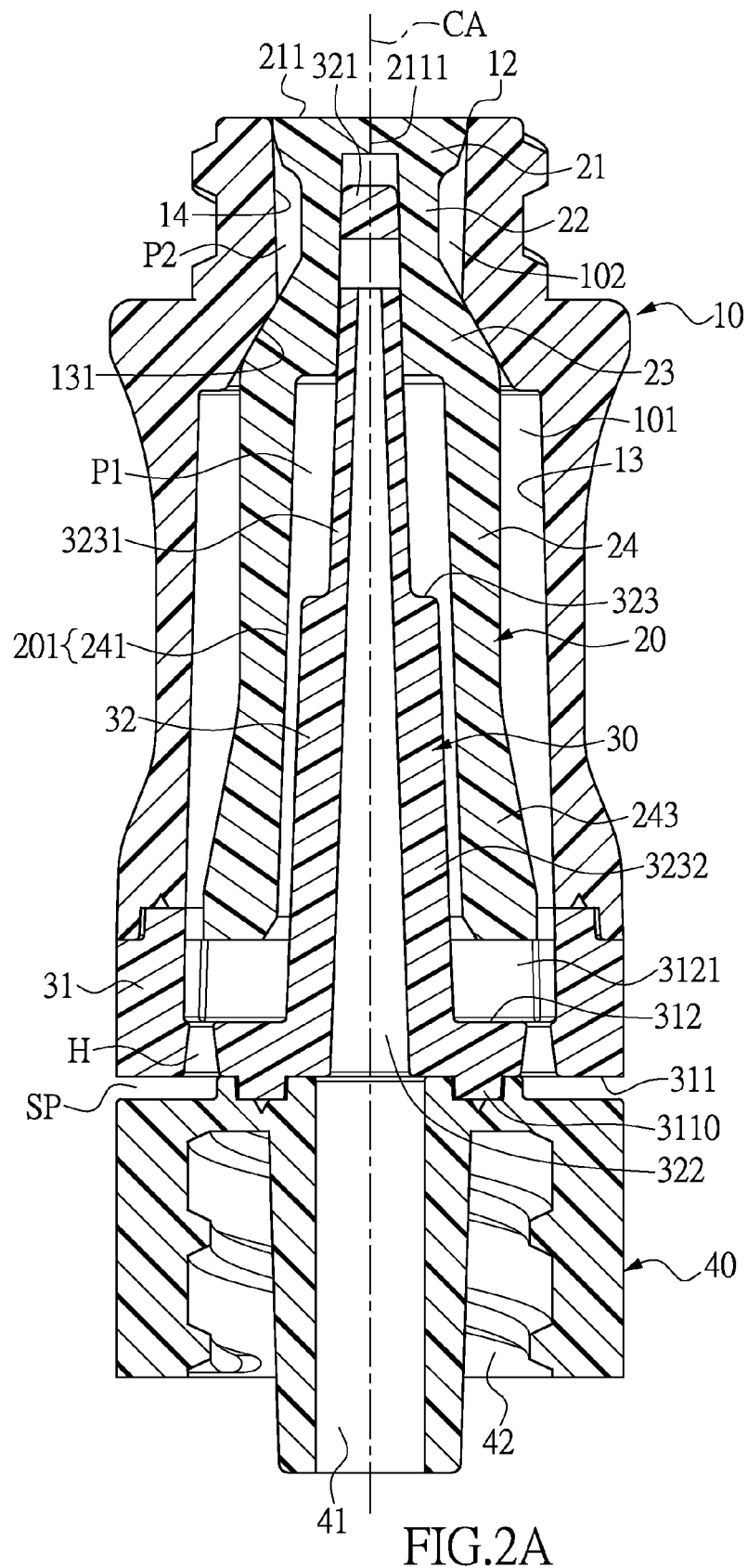
FIG. 2A shows a cross-sectional view of a needleless connector module before actuation according to the present disclosure.

In the second embodiment, the first embodiment is used as a basis and modified upon. As shown in FIG. 2A, the waist platform 323 of the guiding tube 32 can be absent, such that the outer wall of the guiding tube 32 has no protrusions, and the guiding tube 32 thickens from the first guiding opening 321 to the second guiding opening 322 (the abovementioned features are not shown in the figure), therefore the thickening can still produce the effect of the waist platform 323 of the first embodiment to drive the elastic valve 20 to press back against the injection tube SY. The waist platform 323 is absent, so the first compression space P1 is also absent. Specifically, under the first usage condition, the inner wall of the hollow head portion 21 of FIG. 2A is still encloses the guiding tube narrow portion 3231, such that the first guiding opening 321 is hidden in the airtight seam 2111. Under the second usage condition, referring to FIG. 2B which shows the injection tube SY pressing downward on the top surface 211, the hollow head portion 21 is pressed downward, but since the waist platform 323 can be absent, the valve inner wall 201 does not abut the waist platform 323 but still abuts the guiding tube (not shown in the figure) whose diameter increases from the first guiding opening 321 to the second guiding opening 322, such that the first guiding opening 321 is exposed outside the airtight seam 2111, and such that the first guiding opening 321 can be connected to an injection opening (label omitted) of the injection tube SY. Technical features other than the waist portion 323 can refer to those of the first embodiment and are not further detailed herein.

Third Embodiment

Figure 4:
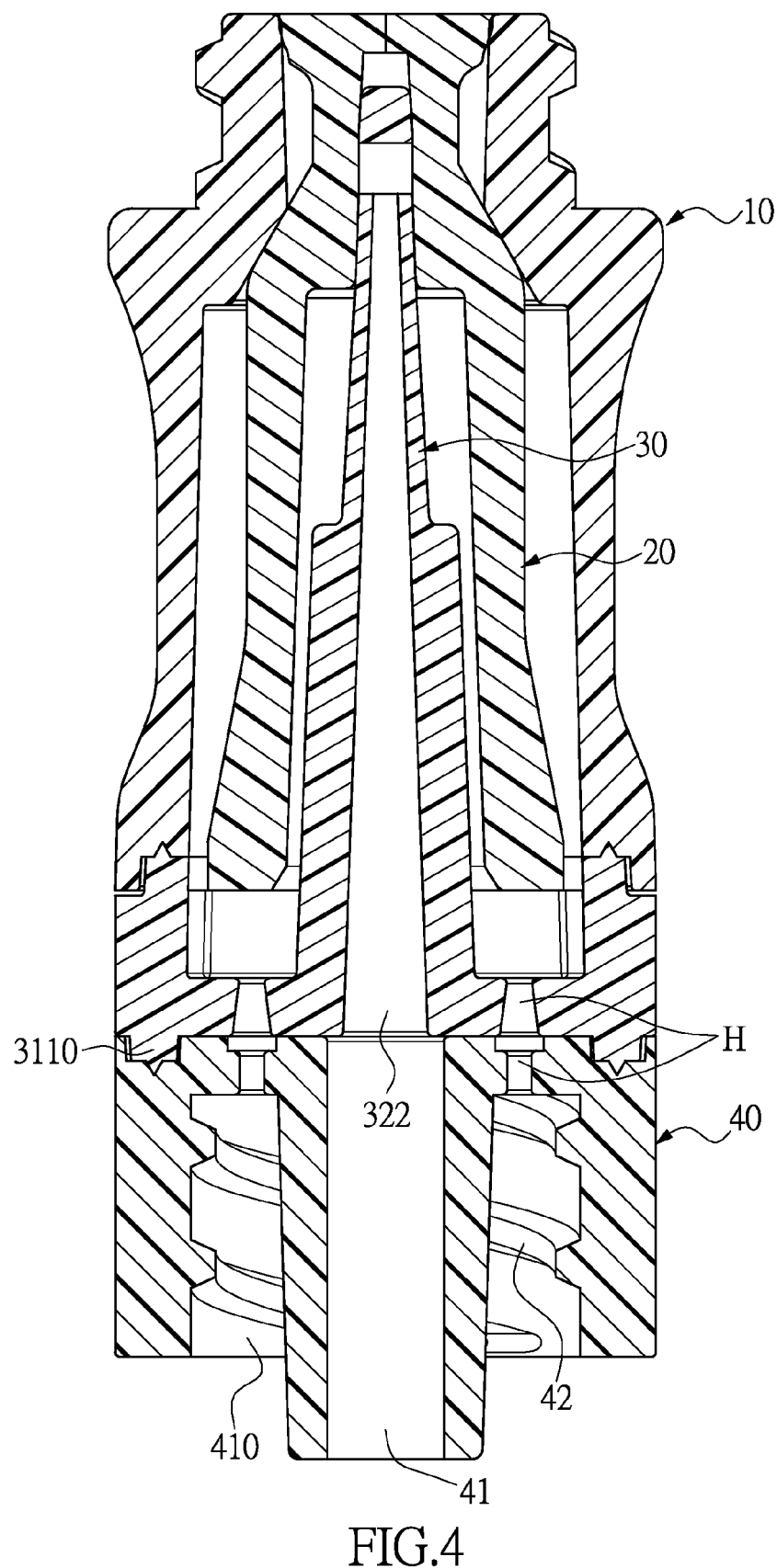
FIG. 4 shows a cross-sectional view of a needleless connector module minus the welded portion before actuation according to the present disclosure.

The present disclosure provides a needleless connector module, based upon the first embodiment. The sleeve tube 10 and the elastic valve 20 are essentially similar to those of the first embodiment and are not further described. However, in the present embodiment, referring to FIG. 1B, FIG. 2A and FIG. 2C, the welded portion 3110 on the flow guiding unit 30 does not exist. Specifically, referring to FIG. 4, in the present embodiment, the flow guiding unit 30 includes: a bottom cover main body 31, a waist platform 323 and a plurality of bottom cover ribs 3121. The bottom cover main body 31 has an upper guiding tube 32' passing from an outer face 311 of the bottom cover main body 31 to an inner face 312 of the bottom cover main body 31. The upper guiding tube 32' protrudes and extends from the inner face 312. The upper guiding tube 32' has a first guiding opening 321. Additionally, the bottom cover main body 31 is formed with a guiding hole H passing from the outer face 311 to the inner face 312.

The waist platform 323 is formed at the outer wall of the upper guiding tube 32'. The waist platform 323 and the first guiding opening 321 define an upper guiding tube narrow portion 3231' therebetween. The waist platform 323 and the inner face 312 define an upper guiding tube wide portion 3232' therebetween. The plurality of bottom cover ribs 3121 is formed on the inner face 312. The elastic valve 20 sleeves the upper guiding tube 32. The hollow shoulder portion 23 abuts the slanted retaining wall 131, such that the elastic valve 20 and the flow guiding unit 30 are assembled together in the sleeve tube 10, and such that the first opening 11 is sealed by the bottom cover main body 31. Selectively under a first usage condition, the inner wall of the hollow head portion 21 encloses the upper guiding tube narrow portion 3231', thereby the first guiding opening 321 is hidden in the airtight seam 2111. Under a second usage condition, the injection tube SY abuts the top surface 211 of the elastic valve 20 as shown in FIG. 2B, such that the hollow head portion 21 is pressed downward, driving the valve inner wall 201 to abut the waist platform 323, and such that the first guiding opening 321 is exposed outside the airtight seam 2111, thereby the first guiding opening 321 can be connected to an injection opening (label omitted) of the injection tube SY.

Preferably, a lower guiding tube 32" extends from the upper guiding tube 32' through the outer face 311 of the bottom cover main body 31. The lower guiding tube 32" has a second guiding opening 322. A screw connection portion 33 is formed around the lower guiding tube 32". A gap SP exists between the screw connection portion 33 and the outer surface 311. The gap SP is in fluid communication with the guiding hole H. The lower guiding tube 32" is for being in fluid communication with an external tubing (not shown in the figures) together with the screw connection portion 33. Therefore, the present embodiment is a three-unit needleless connector module including a sleeve tube 10, an elastic valve 20 and a flow guiding unit 30. The lower guiding tube 32" and the screw connection portion 33 extending from the flow guiding unit 30 can be formed by injection molding to be integrally formed as one body, as opposed to first and second embodiments which requires a welded portion (label omitted) to connect to external units. Other than the screw connection portion 32" and the lower guiding tube 32" formed integrally as one body, the other technical features can be referenced by the first and second embodiments.

Fourth Embodiment

Figure 2B:
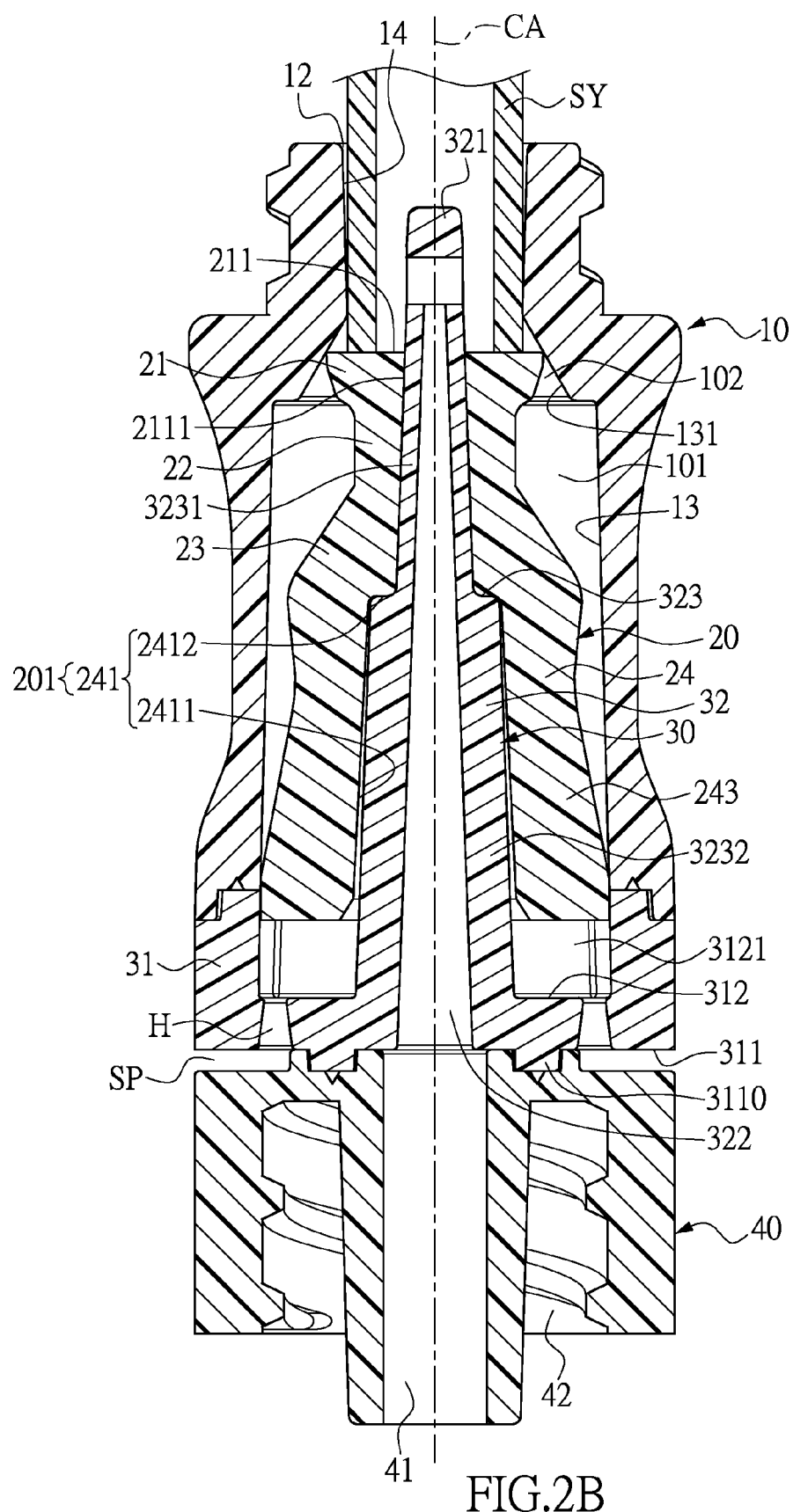
FIG. 2B shows a cross-sectional view of a needleless connector module after actuation according to the present disclosure.
Figure 5:
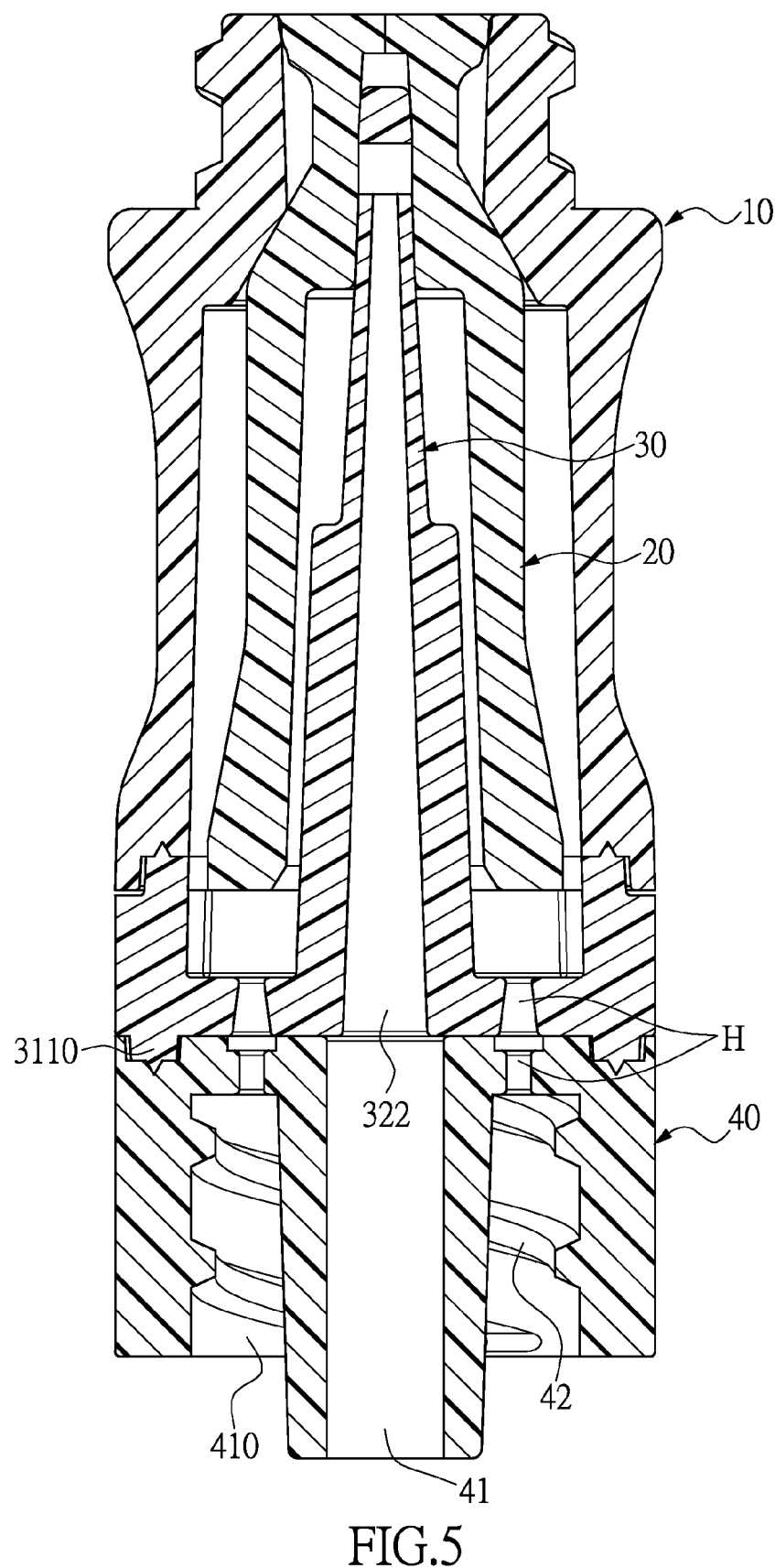
FIG. 5 shows a cross-sectional view of a needleless connector module minus the gap before actuation according to the present disclosure.

Referring to FIG. 2B and FIG. 5, FIG. 5 is a modification upon the first embodiment with the main difference being that when the extension unit 40 is connected to the outer face 311 through the welded portion 3110, the main tubing 41 can still be in fluid communication with the second guiding opening 322, but the extension unit 40 and the outer face 311 do not have a gap SP therebetween as shown in FIG. 2B and are instead in contact with each other. If the extension unit 40 is embodied by a screw-type extension unit, the main tubing 41 can be surrounded by an external space 410. The guiding hole H passes through the top portion of the extension unit 40 in contact with the outer face 311 and is in fluid communication with the external space 410. The main tubing 322 can be surrounded by a screw connection portion 33. The external space 410 is between the screw connection portion 33 and the main tubing 322. Therefore, the guiding hole H does not need to be in fluid communication with the exterior through the gap SP of FIG. 2B. The guiding hole H is in fluid communication with the external space 410, likewise assisting sterilization. Additionally, the extension unit 40 of the present embodiment is not limited to screw-type extension u nits. The extension unit 40 of the present embodiment can take on other forms.

In summary of the above, the needleless connector module of the present disclosure has the following advantages. Through the waist platform protruding from the outer wall of guiding tube of the flow guiding unit, when the elastic valve abuts the waist platform, the waist platform pushes back to increase the press-back effect of the elastic valve on the injection tube, achieving a superb anti-leakage effect.

Through the waist platform protruding from the outer wall of guiding tube of the flow guiding unit, when the elastic valve abuts the waist platform, the waist platform pushes back so that when the injection tube is removed, the elastic valve is restored of its shape, thereby increasing the life span of the elastic valve.

Through the bottom cover ribs, the guiding hole and the gap, pressurized steam can easily enter the interior of the present disclosure during sterilization, thereby properly sterilizing biohazard material.

Through the bottom cover ribs, the strength of the bottom cover main body is increased, such that ultrasonic waves welding different types of extension units can have a high yield rate of good production.

The descriptions illustrated supra set forth simply the preferred embodiments of the present disclosure; however, the characteristics of the present disclosure are by no means restricted thereto. All changes, alternations, or modifications conveniently considered by those skilled in the art are deemed to be encompassed within the scope of the present disclosure delineated by the following claims.

What is claimed is:

1. A needleless connector module comprising:
a sleeve tube having a first opening formed at the lower end of the sleeve tube, and a second opening and a first inner wall formed at the upper end of the sleeve tube, wherein the first inner wall tapers toward the upper end of the sleeve tube and a slanted retaining wall is defined at the upper end of the first inner wall, a second inner wall extends from the slanted retaining wall toward the upper end of the sleeve tube, the slanted retaining wall and the second inner wall define an upper compartment, and the first inner wall defines a lower compartment;
an elastic valve having a valve inner wall and including, from top to bottom, a hollow head portion, a hollow shoulder portion, and a hollow base portion, wherein the upper compartment is configured to accommodate the hollow head portion, the lower compartment is configured to accommodate the hollow base portion, the hollow base portion tapers toward the hollow head portion and the hollow shoulder portion is formed therebetween, a top surface of the hollow head portion is formed with an airtight seam, and the top surface is configured to abut an injection tube;
a flow guiding unit including:
a bottom cover main body having a guiding tube passing from an outer face of the bottom cover main body to an inner face of the bottom cover main body, wherein the guiding tube protrudes and extends from the inner face, the guiding tube has a first guiding opening, the guiding tube is in fluid communication with a second guiding opening at the outer face, and the bottom cover main body is formed with a guiding hole passing from the outer face to the inner face;
a welded portion positioned on the outer face;
a waist platform formed at the outer wall of the guiding tube, wherein the waist platform and the first guiding opening define a guiding tube narrow portion therebetween, and the waist platform and the inner face define a guiding tube wide portion therebetween; and
a plurality of bottom cover ribs formed on the inner face, wherein the plurality of bottom cover ribs protrude from the inner face, the bottom of the elastic valve abuts an upper part of the plurality of bottom cover ribs to prevent the bottom of the elastic valve contacting the inner face, the plurality of bottom cover ribs are spaced apart from each other, so that a plurality of intervals are formed between the plurality of bottom cover ribs; and
an extension unit having at least a main tubing and connected to the outer face through the welded portion, wherein the main tubing is in fluid communication with the second guiding opening, a gap exists between the extension unit and the outer face, the gap, the guiding hole, and the intervals between the plurality of bottom cover ribs are in fluid communication for guiding a steam for sterilizing to enter into a region between the elastic valve and the guiding tube from under the elastic valve; wherein the elastic valve sleeves the guiding tube, the hollow shoulder portion abuts the slanted retaining wall, the elastic valve and the flow guiding unit are assembled together in the sleeve tube, and the first opening is sealed by the bottom cover main body, wherein under a first usage condition, the inner wall of the hollow head portion encloses the guiding tube narrow portion, and the first guiding opening is hidden in the airtight seam; and under a second usage condition, the injection tube abuts the top surface, the hollow head portion is pressed downward, driving the valve inner wall to abut the waist platform, the first guiding opening is exposed outside the airtight seam, and the first guiding opening is connected to an injection opening of the injection tube.

2. The needleless connector module according to claim 1, wherein the valve inner wall includes a base portion inner wall formed at the hollow base portion, and under the second usage condition the base portion inner wall abuts the waist platform.

3. The needleless connector module according to claim 2, wherein the base portion inner wall includes a side base portion inner wall and an interference inner wall, the interference inner wall extends from the side base portion inner wall toward the longitudinal central axis of the sleeve tube and is proximal to the hollow shoulder portion, and under the second usage condition, the interference inner wall abuts the waist platform.

4. The needleless connector module according to claim 3, wherein under the first usage condition, a first compression space is defined in the hollow base portion and between the interference inner wall, a portion of the side base portion inner wall, the waist platform and the guiding tube narrow portion.

5. The needleless connector module according to claim 4, wherein the other portion of the side base portion inner wall encloses the guiding tube wide portion, the end of the hollow base portion proximal to the bottom cover main body is a valve base portion opening abutting the bottom cover ribs.

6. The needleless connector module according to claim 5, wherein an expansion portion extending away from the central axis of the sleeve tube at a portion of the hollow base portion proximal to the bottom cover main body, and under the second usage condition the expansion portion abuts the inner wall of the sleeve tube.

7. The needleless connector module according to claim 1, wherein the inner wall or the outer wall of the elastic valve is a rough structure of granulated indentations formed through sandblasting.

8. The needleless connector module according to claim 1, wherein the flow guiding unit and the elastic valve have a layer of silicone oil therebetween.

9. The needleless connector module according to claim 1, wherein a hollow neck portion is formed between the hollow head portion and the hollow shoulder portion, the outer wall of the hollow neck portion contracts toward the central axis of the sleeve tube relative to the hollow head portion and the hollow shoulder portion, and the hollow neck portion and the inner wall of the upper end of the sleeve tube define a second compression space therebetween.

10. The needleless connector module according to claim 1, wherein the main tubing is surrounded by a screw connection portion for connecting to external tubing.

11. The needleless connector module according to claim 1, wherein the main tubing is formed with a plug portion for tightly plugging to external tubing.

12. The needleless connector module according to claim 11, wherein the portion of the main tubing between the plug portion and the end proximal to the second guiding opening is connected to a branch tubing, and the branch tubing and the main tubing form a Y-shaped or a T-shaped structure.

* * * * *